(12) United States Patent
Spalding

(10) Patent No.: US 7,744,575 B1
(45) Date of Patent: Jun. 29, 2010

(54) SANITARY NAPKIN WITH ATTACHMENT STRAPS

(76) Inventor: Jennifer Spalding, 11448 Deerfield Dr., #2, Truckee, CA (US) 96161

( * ) Notice: Subject to any disclaimer, the term of this patent is extended or adjusted under 35 U.S.C. 154(b) by 0 days.

(21) Appl. No.: 11/260,594

(22) Filed: Oct. 27, 2005

Related U.S. Application Data

(60) Provisional application No. 60/623,139, filed on Oct. 27, 2004.

(51) Int. Cl.
*A61M 13/15* (2006.01)
(52) U.S. Cl. ............... 604/385.01; 604/385.03; 604/386; 604/389; 604/385.05
(58) Field of Classification Search ............ 604/385.01, 604/385.03, 386, 389, 385.05, 402
See application file for complete search history.

(56) References Cited

U.S. PATENT DOCUMENTS

| | | | |
|---|---|---|---|
| 4,573,986 A | 3/1986 | Minetola |
| 4,589,876 A | 5/1986 | Van Tilburg |
| 4,609,518 A | 9/1986 | Curro et al. |
| 4,629,643 A | 12/1986 | Curro |
| 4,687,478 A | 8/1987 | Van Tilburg |
| 4,892,534 A | 1/1990 | Datta |
| 4,900,320 A | 2/1990 | McCoy |
| 4,950,264 A | 8/1990 | Osborn |
| 5,009,653 A | 4/1991 | Osborn |
| 5,234,422 A | 8/1993 | Sneller |
| 5,267,992 A | 12/1993 | Van Tilburg |
| 5,295,984 A | 3/1994 | Contente |
| 5,308,346 A | 5/1994 | Sneller et al. |
| 5,346,486 A | 9/1994 | Osborn |
| 5,354,400 A | 10/1994 | Lavash |
| 5,389,094 A | 2/1995 | Lavash |
| 5,413,568 A | 5/1995 | Roach |
| 5,489,283 A | 2/1996 | Van Tilburg |
| 5,520,875 A | 5/1996 | Wnuk |
| 5,569,231 A | 10/1996 | Emenaker |
| 5,620,430 A | 4/1997 | Bamber |
| 5,683,373 A | 11/1997 | Darby |
| 5,704,930 A | 1/1998 | Lavash |
| 5,713,886 A | 2/1998 | Sturino |
| 5,800,654 A | 9/1998 | Davis |
| 6,004,893 A | 12/1999 | Van Tilburg |
| 6,087,551 A | 7/2000 | Pereira |
| 6,093,178 A | 7/2000 | Osborn |
| 6,200,298 B1 | 3/2001 | Osborn |
| 6,231,555 B1 | 5/2001 | Lynard et al. |
| 6,287,288 B1 | 9/2001 | Osborn |
| 6,458,112 B1 | 10/2002 | Marshall |
| 6,503,233 B1 | 1/2003 | Chen |
| 6,586,653 B2 | 7/2003 | Graeme |
| 6,626,879 B1 | 9/2003 | Ashton |
| 6,632,210 B1 | 10/2003 | Glasgow |
| 6,635,799 B1 | 10/2003 | Osborn |
| 6,740,069 B2 | 5/2004 | Drevik |
| 6,746,435 B1 | 6/2004 | Van Tilburg |

(Continued)

*Primary Examiner*—Jacqueline F. Stephens

(57) ABSTRACT

The present invention is directed to a wearable sanitary napkin having a front panel having an absorbent sanitary napkin and one or more straps for attachment to the body. In one embodiment, the front panel is substantially triangular in shape and the straps are connected to the corners of the triangle to form a thong style underwear. In still another embodiment, the wearable sanitary napkins are made of inexpensive material so that they are disposable. The absorbent sanitary napkins panties can be made with different levels of absorptive capacity and can be in different configurations and designs.

3 Claims, 2 Drawing Sheets

U.S. PATENT DOCUMENTS

| | | | |
|---|---|---|---|
| 2003/0078554 A1* | 4/2003 | Drevik | 604/385.03 |
| 2004/0102747 A1* | 5/2004 | Bell et al. | 604/358 |
| 2005/0267438 A1* | 12/2005 | Lee | 604/396 |
| 2006/0074392 A1 | 4/2006 | Sava | |

* cited by examiner

SANITARY NAPKIN WITH ATTACHMENT STRAPS

RELATED APPLICATION INFORMATION

This patent claims priority to U.S. Provisional Patent Appln. No. 60/623,139 filed on Oct. 27, 2004, which is incorporated herein by reference in its entirety.

TECHNICAL FIELD

This invention relates to absorbent devices. More particularly, it relates to sanitary napkins that have attachment straps for the body.

BACKGROUND OF THE INVENTION

Sanitary napkins are absorbent devices designed to receive and contain vaginal discharges, such as menses, spotting, and leaking bladders. They are omnipresent items of modern society. In recent periods disposable sanitary napkins designed to be held adjacent to the human body through the agency of a garment, such as an undergarment or panty, have effectively supplanted the more traditional type of sanitary napkin, which required a specially designed belt for use.

The choices for women today are essentially limited to tampons, which larger sanitary napkins worn in the underwear, or adhesive pads which can be applied to the inside surface of the undergarment. These pads can leave the user with soiled undergarments, bunching, gathering and other discomforts and inconvenience.

In recent years, in part as a result of these problems, sanitary napkins have evolved to be thinner and more flexible. For example, some sanitary napkins have wings to aid attachment to the underwear and help prevent soiling, and others are provided with different colors to match clothing. Sanitary napkins are also available in various shapes and sizes, e.g., even in a shape to fit thong style underwear. These sanitary napkins are generally triangular in shape, essentially matched to the triangular shape of the front/bottom area of the thong style underwear, wherein the sides of the triangle typically extend out to the thighs. However, such sanitary napkins move around or require some mechanism to attach the sanitary napkin to the underwear, e.g., an adhesive backing or extending wings structures for wrapping around the underwear.

There is, therefore, a need for a sanitary napkin that can be easily used. There is also a need for a sanitary napkin that can be maintained in the proper placement.

SUMMARY OF THE INVENTION

It is therefore an object of the present invention to provide a wearable sanitary napkin that can be properly positioned and maintained by the user. These and other objects, advantages and features of the invention will become apparent from the following description of a preferred embodiment, considered along with the drawings.

In one embodiment, the present invention is directed to a wearable sanitary napkin having (1) a front panel including an absorbent sanitary napkin, and (2) one or more straps attached to the front panel for positioning and maintaining the absorbent sanitary napkin on the user. The size and shape of the absorbent sanitary napkin can be chosen to be complementary to any portion of the front panel. It is preferred to have a front panel that is substantially triangular with a base of the triangle situated towards the hips and the apex of the triangle situated near the rear of the user.

In another embodiment, the absorbent sanitary napkin forms part or all of the front panel. In this embodiment, part of the front panel can be made of one material and part of the front panel can be the absorbent sanitary napkin.

In another embodiment, one end of a hip strap is attached to one corner at the base of the substantially triangular front panel and the other end of the hip strap is attached to the other corner at the base of the substantially triangular front panel, and one end of a rear strap is attached to the apex of the substantially triangular front panel and the other end of the rear strap is attached to the hip strap near the middle of the hip strap.

In still another embodiment, the front panel is attached to a hip strap in the shape of a circular loop, and one end of a rear strap is attached to the apex of the substantially triangular front panel and the other end of the rear strap is attached to the hip strap near the middle of the portion of the hip strap that is not attached to the front panel.

DETAILED DESCRIPTION OF THE INVENTION

Figure 1:
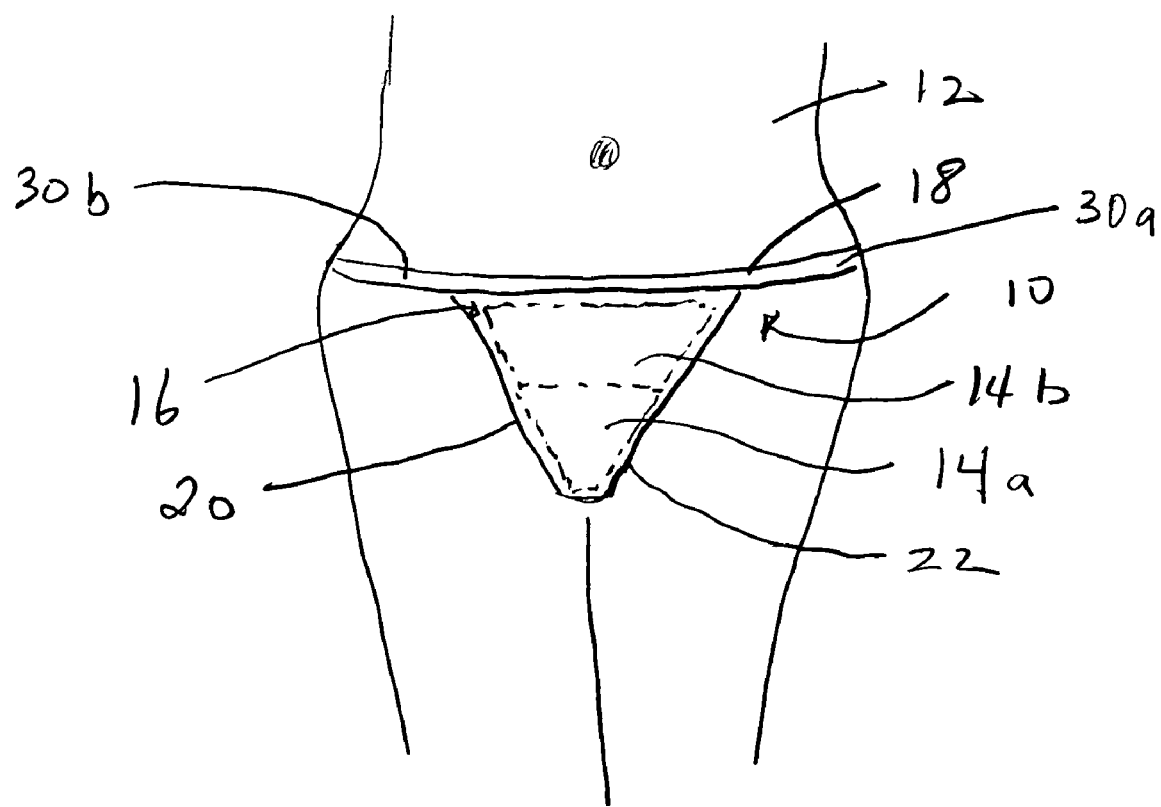
FIG. 1 is a frontal view of a wearable sanitary napkin according to the invention, as worn on a woman's body.

The present invention is directed to a wearable sanitary napkin. The wearable sanitary napkin includes (i) a front panel having an absorbent sanitary napkin and (ii) one or more straps attached to the front panel for positioning and maintaining the absorbent sanitary napkin. The one or more straps allow the user to wear the wearable sanitary napkin in the same way as underwear is worn.

The front panel preferably has a substantially triangular shape and the straps are attached to the corners of the substantially triangular front panel, wherein the base of the triangle is situated toward the hips and the apex of the triangle is situated near the rear of the user when worn. The front panel is most preferably shape to be substantially an equilateral triangle or substantially an isosceles triangle. More preferably, the front panel and the straps are arranged to form a thong style underwear. The term "substantially triangular," as used herein, means resembling a triangle. For example, it is contemplated that substantially triangular shapes can include one or more of the following: round corners, elongated corners, curved sides in either the convex and/or concave direction, and combinations thereof.

It is believed that the substantially triangular shape of the wearable sanitary napkin is more conducive to fitting the natural anatomical shape of a woman's body, thereby providing a more comfortable fit. It is also believed that the anatomical correctness of the substantially triangular shape of the wearable sanitary napkin helps to prevent leaking of vaginal fluids by providing a better fit to the body. As a result, the wearable sanitary napkin will not slip off or slide away from the correct position, thereby preventing leaks and stained clothing associated with stick-on sanitary napkins. Furthermore, since the absorbent sanitary napkin is associated with or incorporated in the front panel, the use of releasable adhesives, typically used in stick-on sanitary napkins, is eliminated, thereby removing any potential health problems resulting from contacting the skin with such adhesives. Thong style underwear has also gained increasing popularity for the fashionable appearance (e.g., prevents unsightly look of panty lines) as well as for comfort. For example, it is believed that thong style underwear does not wrap unduly tightly around the thighs and allow for more freedom of movement and comfort.

The wearable sanitary napkins of the present invention can be made of any materials known in the art. It is preferred, however, to utilize inexpensive materials so that the wearable sanitary napkins can be disposable. It is also preferable to use woven or non-woven materials, such as a fabric of woven inexpensive cellulose fibers, having a look and feel similar to cloth. It is most preferred to use cotton or cotton-like materials to increase breathability and hygiene, especially for the hems and/or linings. Other inexpensive fabrics can be used. Because small amounts of materials, such as fabric, are required, the cost of manufacture is considerably decreased, thereby helping to make them disposable. In one embodiment the wearable sanitary napkins are formed of cotton or they may be made from other popular but inexpensive fabrics such as Nylon, Spandex or a combination of the two, or a paper product.

Referring now to the drawings, FIG. 1 illustrates one embodiment of a wearable sanitary napkin 10 having a front panel 16 and one or more straps (30a, 30b) in accordance with the invention as worn on a woman's torso 12. The wearable sanitary napkin may be in different colors and different patterns, as is known in the art. The front panel can be made of cloth or any cloth-like material.

The front panel 16 of FIG. 1 includes an absorbent sanitary napkin 14a (shown in dashed lines). The size and shape of the absorbent sanitary napkin 14 can be chosen to be complementary to any portion of the front panel. See for example sanitary napkin 14a, which is a portion of the front panel 16, and sanitary napkin 14b, which is substantially the same size and shape as the front panel. The sanitary napkin 14 can be at least 25% of the surface area of the front panel 16, preferably at least 33% of the surface area of the front panel 16, and more preferably at least 50% of the surface area of the front panel. By changing the size and shape of the absorbent sanitary napkin 14, different levels of absorptive capacity and be provided in different configurations and designs. The drawing is not to scale and does not necessarily indicate precisely the region where the sanitary napkin 14 will be located, but it is generally positioned approximately where traditional prior art sanitary napkins are placed inside the underwear. The front panel can be made of a single sheet of material to which the absorbent sanitary napkin 14 is attached. Alternatively, the front panel can be made of two sheets of the same or different material to form a pocket in which the absorbent sanitary napkin 14 is inserted. In this alternative, it is preferred to attach the sanitary napkin 14 to the outer sheet of material (e.g., away from the body when worn). For the sheet that will be in contact with the body, it is further preferred to use a porous material, e.g., gauze or any other suitable material known in the art.

In the embodiment illustrated in FIG. 1, the absorbent sanitary napkin 14 forms an integral part of front panel 16. Any method known in the art may be used to attach absorbent sanitary napkin 14 to front panel 16 or encapsulate absorbent sanitary napkin 14 in front panel 16. For example, the absorbent sanitary napkin 14 may be stitched to the interior side of a front panel 16. The absorbent sanitary napkin may also be attached into an opening in the panty fabric extending through the front area where absorption is needed. If appropriate materials are used, heat bonding or ultrasonic bonding can be used instead of stitching or other mechanical attachment. In another embodiment the absorbent sanitary napkin 14 may actually form a portion of the front panel or take the place of the front panel, wherein it is secured to the remainder of the fabric, if any, such as by stitching around the edges the absorbent pad 14. The absorbent sanitary napkin 14 can thus fill a large opening, which would otherwise be left in the remaining fabric of front panel 16. There may be one or more hems around the wearable sanitary napkin, such as at 18, 20 and 22, and thus a strip of fabric or expandable material may extend down around these lines 20 and 22 to the back of the front panel 16, secured to edges of the absorbent sanitary napkin 14 if the sanitary napkin 14 forms the fill-in panel as just described.

The wearable sanitary napkins of the present invention also include one or more straps. Although not required, the straps are preferably elastic. The straps can be attached to front panel 16 by any known process or method known in the art. For example, many of the process described in the patents listed below for the absorbent sanitary napkin 14 can be used to attach the straps to front panel 16. Furthermore, the straps can be made to be releasable and reattachable, as also described in many of the patents listed below. The straps can also be any desirable cross sectional shape, including a round shape (e.g., a string) or a flat shape (e.g., a strip of material).

Figure 2:
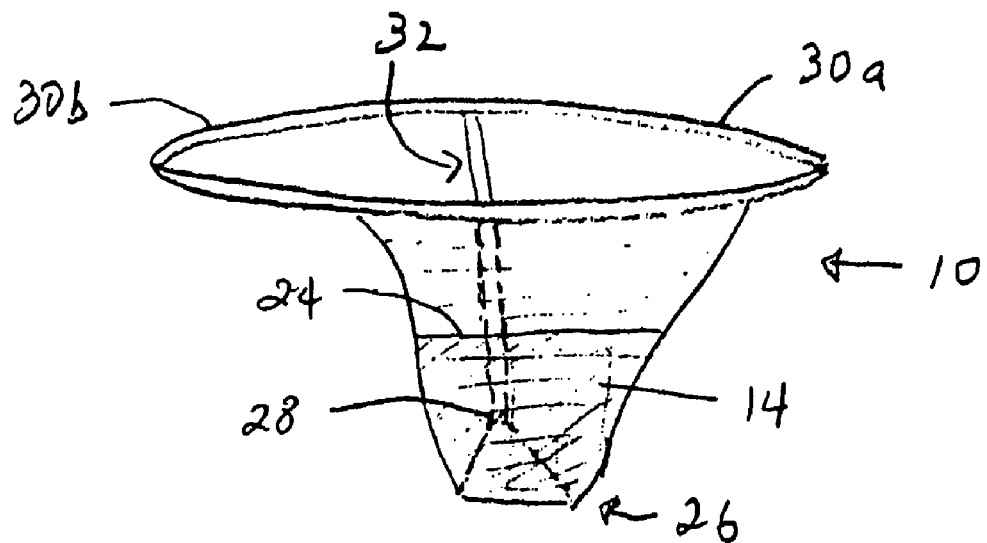
FIG. 2 is a perspective view showing an embodiment of the wearable sanitary napkin.

In the embodiment illustrated in FIGS. 1 and 2, one strap is used to serve as a hip strap (30a, 30b) to which the front panel 16 is attached. Furthermore, FIG. 2 illustrates one end of a rear strap 32 connected to the hip strap (30a, 30b) and the other end of the rear strap 32 connected to the bottom portion 28 of the front panel.

In another embodiment, one end of a hip strap (e.g., 30a) can be attached to the upper right corner of the front panel 16 and the other end of the hip strap (e.g., 30b) can be attached to the upper left corner of the front panel. In this embodiment, a rear strap 32 can then be used to connect the hip strap (30a, 30b) to the bottom portion 28 of the front panel In still another embodiment, one end of a first strap (e.g., 30a) can be attached to the upper right corner of the front panel 16, and the other end of the first strap can be attached to the bottom corner 28 of the front panel 16. In this embodiment, one end of a second strap (e.g., 30b) can be attached to the upper left corner of the front panel 16, and the other end of the second strap can be attached to the bottom corner 28 of the front panel 16. In this embodiment, it is preferred to combine a portion of the first and second straps into a single strap near the bottom corner 28, e.g., for 2.5-6 cm from the bottom corner.

FIG. 2 further illustrates a wearable sanitary napkin 10, and indicates the absorbent sanitary napkin portion 14 of the wearable sanitary napkin 10. In this embodiment the absorbent sanitary napkin portion extends from a line 24 in front panel 16 and extends down into the crotch area, indicated at 26, and partially around into the narrow back portion 28 seen in dashed lines) of the wearable sanitary napkin 10. The absorbent portion is shown ending at a line at the rear/bottom point 28 of the front panel.

Figure 3:
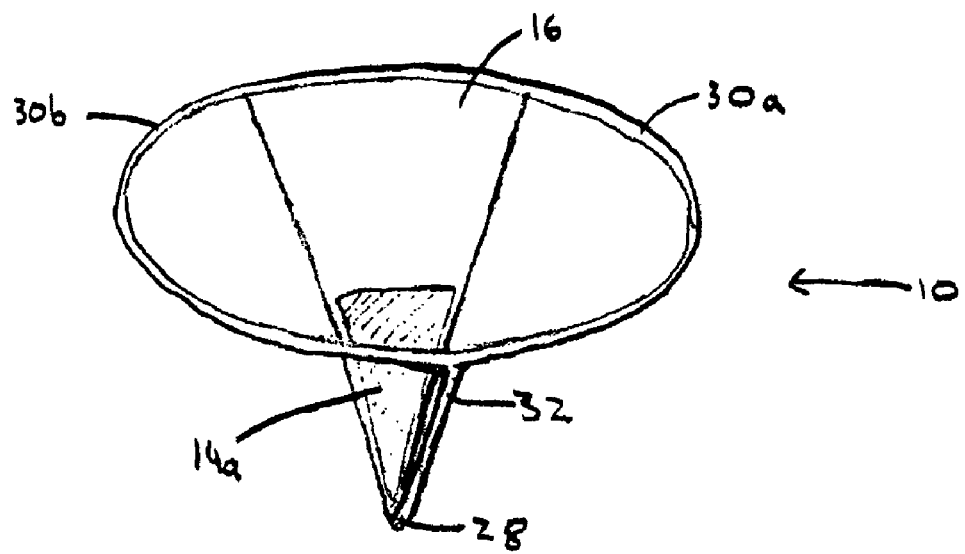
FIG. 3 is a top perspective view showing an embodiment of the wearable sanitary napkin.

FIG. 3 shows an absorbent pad or panel 14a secured to the front panel 16 of wearable sanitary napkin 10. The absorbent section of 14a can be attached to the fabric of the front panel 16 by stitching or other means, or the absorbent section of 14a may take the place of a front panel 16, or a portion of the front panel 16. The absorbent sanitary napkin may be stitched or otherwise attached into an opening in the panty fabric extending through the front area where absorption is needed. If appropriate materials are used, heat bonding or ultrasonic bonding can be used instead of stitching or other mechanical attachment.

The pad may be constructed, for example, in the manner known in the art, or its absorbent structure can be constructed as in the popular off-the-shelf products CAREFREE THONG or ALWAYS ULTRA THIN. Typically the pad has a back sheet that is substantially impervious to moisture, the back sheet being the outer side as worn. The absorbent sanitary napkin may be of several varieties, such as disclosed in any of the following U.S. patent Nos., which are all incorporated by reference herein in their entirety: U.S. Pat. No. 4,573,986 to Minetola et al.; U.S. Pat. No. 4,589,876 to Van Tilburg; U.S. Pat. No. 4,609,518 to Curro et al.; U.S. Pat. No. 4,629,643 to Curro et al.; U.S. Pat. No. 4,687,478 to Van Tilburg; U.S. Pat. No. 4,892,534 to Datta et al.; U.S. Pat. No. 4,900,320 to McCoy; U.S. Pat. No. 4,950,264 to Osborn, III; U.S. Pat. No. 5,009,653 to Osborn, III; U.S. Pat. No. 5,234,422 to Sneller et al.; U.S. Pat. No. 5,267,992 to Van Tilburg; U.S. Pat. No. 5,308,346 to Sneller et al.; U.S. Pat. No. 5,346,486 to Osborn, III et al.; U.S. Pat. No. 5,354,400 to Lavash et al; U.S. Pat. No. 5,389,094 to Lavash et al.; U.S. Pat. No. 5,413,568 to Roach et al.; U.S. Pat. No. 5,489,283 to Van Tillburg; U.S. Pat. No. 5,520,875 to Wnuk et al; U.S. Pat. No. 5,569,231 to Emenaker et al.; U.S. Pat. No. 5,620,430 to Bamber; U.S. Pat. No. 5,704,930 to Lavash et al.; U.S. Pat. No. 5,800,654 to Davis et al.; U.S. Pat. No. 6,004,893 to Van Tilburg; U.S. Pat. No. 6,087,551 to Pereira; U.S. Pat. No. 6,093,178 to Osborn, III, et al.; U.S. Pat. No. 6,200,298 to Osborn, III, et al.; U.S. Pat. No. 6,231,555 to Lynard et al.; U.S. Pat. No. 6,287,288 to Osborn, III, et al.; U.S. Pat. No. 6,458,112 to Marshall, III, et al.; U.S. Pat. No. 6,503,233 to Chen et al.; U.S. Pat. No. 6,586,653 to Graeme, III, et al.; U.S. Pat. No. 6,632,210 to Glasglow et al.; U.S. Pat. No. 6,635,799 to Osborn, III, et al.; U.S. Pat. No. 6,740,069 to Drevik; and U.S. Pat. No. 6,746,435 to Van Tilburg.

The wearable sanitary napkins of the present invention can be used to receive and contain vaginal discharges by wearing them in a similar fashion to wearing normal underwear. The wearable sanitary napkins can be worn by themselves or in conjunction with another feminine hygiene product, such as tampons. Furthermore, the wearable sanitary napkins can be work as underwear by themselves, or securely underneath regular underwear or nylons.

The above-described preferred embodiments are intended to illustrate the principles of the invention, but not to limit its scope. Other embodiments and variations to this preferred embodiment will be apparent to those skilled in the art and may be made without departing from the spirit and scope of the invention as defined in the following claims.

The invention claimed is:

1. A disposable, wearable sanitary napkin comprising:
   a substantially triangular front panel having (i) an outer layer with an inner surface; (ii) a permeable inner layer; and (iii) an absorbent sanitary napkin;
   the outer layer and the inner layer being coupled together at their peripheries to form a pocket to receive the absorbent sanitary napkin, the absorbent sanitary napkin thereby being held between the inner surface of the front panel outer layer and the permeable inner layer;
   means for attaching the absorbent sanitary napkin to the inner surface of the front panel outer layer;
   a hip strap in the shape of a circular loop attached to a base of the substantially triangular front panel; and,
   a rear strap having one end attached to an apex of the substantially triangular front panel and the other end of the rear strap attached to the hip strap.

2. The sanitary napkin according to claim 1, wherein means for attaching the absorbent sanitary napkin to the inner surface of the front panel outer layer is selected from a group consisting of stitching, heat bonding and ultrasonic bonding.

3. A disposable, wearable sanitary napkin comprising:
   a substantially triangular front panel having an outer surface and an inner surface, wherein the inner surface is an absorbent sanitary napkin;
   a hip strap in the shape of a circular loop attached to a base of the substantially triangular front panel; and,
   a rear strap having one end attached to the apex of the substantially triangular front panel and the other end of the rear strap is attached to the hip strap.

* * * * *